(12) United States Patent
Eisenach

(10) Patent No.: US 6,248,744 B1
(45) Date of Patent: Jun. 19, 2001

(54) METHOD FOR THE TREATMENT OF PAIN, INCLUDING CHRONIC AND FEMALE SPECIFIC PAIN

(75) Inventor: James C. Eisenach, Winston-Salem, NC (US)

(73) Assignee: Wake Forest University, Winston-Salem, NC (US)

( * ) Notice: Subject to any disclaimer, the term of this patent is extended or adjusted under 35 U.S.C. 154(b) by 0 days.

(21) Appl. No.: 09/622,675

(22) PCT Filed: Feb. 24, 1999

(86) PCT No.: PCT/US99/03896

§ 371 Date: Oct. 5, 2000

§ 102(e) Date: Oct. 5, 2000

(87) PCT Pub. No.: WO99/43322

PCT Pub. Date: Sep. 2, 1999

Related U.S. Application Data

(60) Provisional application No. 60/075,794, filed on Feb. 24, 1998.

(51) Int. Cl.$^7$ .................................................. A61K 31/505
(52) U.S. Cl. ..................... 514/256; 514/277; 514/343; 514/345; 514/351; 514/357; 514/384
(58) Field of Search ..................... 514/256, 277, 514/343, 345, 351, 357, 384

(56) References Cited

U.S. PATENT DOCUMENTS

| | | | | |
|---|---|---|---|---|
| 5,212,188 | * | 5/1993 | Caldwell et al. | 514/343 |
| 5,604,231 | * | 2/1997 | Smith et al. | 514/256 |
| 5,616,716 | * | 4/1997 | Dull et al. | 546/300 |
| 5,663,357 | * | 9/1997 | Teng et al. | 546/323 |
| 5,811,442 | * | 9/1998 | Bencherif et al. | 514/384 |
| 5,861,423 | * | 1/1999 | Caldwell et al. | 514/351 |

\* cited by examiner

*Primary Examiner*—James H. Reamer
(74) *Attorney, Agent, or Firm*—Dann Dorfman Herrell and Skillman, P.C.

(57) ABSTRACT

Patients susceptible to, or suffering from chronic and/or female-specific pain are treated by administering an effective amount of a metanicotine-based compound.

36 Claims, No Drawings

METHOD FOR THE TREATMENT OF PAIN, INCLUDING CHRONIC AND FEMALE SPECIFIC PAIN

This application is a 371 of PCT/US99/03896 filed Feb. 24, 1999 which claim benefit to provisional application No. 60/075,794 filed Feb. 24, 1998.

BACKGROUND OF THE INVENTION

A. Field of the Invention

The present invention relates to a method for treatment of pain and specifically relating to treatment of chronic pain, acute and chronic female specific pain and to methods for preventing disabilities related to such types of pain.

B. Description of Related Art

Pain is associated with a variety of different underlying illnesses or injuries. Pain may be either acute or chronic.

Chronic or intractable pain is often endured over many years or decades. Patients suffering from chronic pain often develop emotional problems which can lead to depression and in the worst case, attempted suicide. Long lasting pain often occurs particularly in joints, in muscles, connective tissue (e.g. fibromyalgia) and in the back. In the United States alone, chronic pain causes a loss of more than 250 million working days per year.

A patient is considered to have chronic pain when complaints thereof last longer than six months. In the course of time, chronic pain can come completely to the fore and form a independent clinical syndrome. Today most of the clinical phenomena of chronic pain syndrome are explained as a permanent excitation of spinal convergence neurons. This exictation can be provoked by either visceral or somatic afferent stimulation.

In general, brain pathways governing the perception of pain are still incompletely understood, although sensory afferent synaptic connections to the spinal cord, termed "nociceptive pathways" have been documented in some detail. In the first leg of such pathways, C- and A-fibers which project from peripheral sites to the spinal cord carry nociceptive signals. Polysynaptic junctions in the dorsal horn of the spinal cord are involved in the relay and modulation of sensations of pain to various regions of the brain, including the periaqueductal grey region (McGeer et al., 1987 *Molecular Neurobiology of the Mammalian Brain*, Plenum Press, NY). Analgesia, or the reduction of pain perception, can be effected directly by decreasing transmission along such nociceptive pathways. Analgesic opiates are thought to act by mimicking the effects of endorphin or enkephalin peptide-containing neurons, which synapse presynaptically at the C- or A-fiber terminal and which, when they fire, inhibit release of neurotransmitters, including substance P. Descending pathways from the brain are also inhibitory on C- and A-fiber firing.

Certain types of pain have complex etiologies. For example, neuropathic pain is generally a chronic condition attributable to injury or partial transection of a peripheral nerve. This type of pain is characterized by hyperesthesia, or enhanced sensitivity to external noxious stimuli. The hyperesthetic component of neuropathic pain does not respond to the same pharmaceutical interventions as does more generalized and acute forms of pain.

Opioid compounds (opiates) such as morphine, while effective in producing analgesia for many types of pain, are not always effective, and may induce tolerance in patients. When a subject is tolerant to opioid narcotics, increased doses are required to achieve a satisfactory analgesic effect. At high doses, these compounds produce side effects, such as respiratory depression, which can be life threatening. In addition, opioids frequently produce physical dependence in patients. Dependence appears to be related to the dose of opioid taken and the period of time over which it is taken by the subject. For this reason, alternate therapies for the management of chronic pain are widely sought after. In addition, compounds which serve as either a replacement for or as an adjunct to opioid treatment in order to decrease the dosage of analgesic compound required, have utility in the treatment of pain, particularly pain of the chronic, intractable type.

Several biochemical mechanisms may be activated by the administration of analgesic drugs to manage pain in humans, depending on the site of action of the drug. One such mechanism operates through local mediators by inhibiting pathways which generate pain-causing substances, such as prostaglandins, at the site of injury. Examples of agents that relieve pain in this way are the non-steroidal anti-inflammatory drugs (NSAIDs) which, as a class, are usually only effective against pain of low to moderate intensity. Moreover, long term use of many NSAIDs produce gastrointestinal side-effects such as ulceration and bleeding. Another mechanism to induce analgesia is through peripheral neurotransmission, such as local anesthetics, which act by blocking nerves that transmit pain signals. These drugs are delivered through injections and block other sensations in addition to pain. High doses of local anaesthetics may also have adverse effects on the heart causing arrhythmias, and in the brain producing convulsions. Pain relief may also be effected through CNS-mediated mechanisms (spinal and supra-spinal mechanisms). A number of attempts have been made to alleviate pain associated with pathological and non-pathological conditions in this way. As mentioned previously, the best known CNS-active analgesics are the narcotic opiates, such as morphine. While they are effective and potent, they often have several detrimental side effects.

Numerous studies of gender-comparative pain have been reported in the medical literature. These studies tend to establish that anatomical and physiological differences play an important role in central cholinergic activity and antinociception. Such studies are reviewed by Unruh, Pain, 65: 123–167 (1996). For example, many women experience non-pathological pain resulting from menstruation (including pre-menstrual pain), ovulation, pregnancy and childbirth. In addition, there are documented differences between the sexes in the prevalence of common recurrent pain such as headache and migraine, facial and oral pain, back pain, musculo-skeletal pain and abdominal pain. Finally, a number of pathological conditions result in greater pain experience in females than in males (Unruh, supra).

Recent reports of the involvement of central nicotinic neurotransmission in analgesia have stimulated the search for nicotinic agonists with analgesic properties. Epibatidine, a minor alkaloid from the South American poison frog Epipedobates tricolor (genus Dendrobatidae), is a potent nicotinic agonist which induces analgesia in rats and mice with a potency three orders of magnitude higher than morphine (Spande et al., J. Am. Chem. Soc., 114: 3475–3478, 1992; Bradley D., Science, 261: 1117, 1993). The analgesic effect of epidatidine appears to be mediated through agonism at CNS (spinal/supraspinal) nicotinic receptors and is independent of opioid release. Epibatidine is a potent agonist of ganglionic nicotinic receptors and elicits cardiorespiratory effects similar to those of nicotine. (Fisher et al., J. Pharmacol. Exp. Therap., 207: 702–707, 1994), severely limiting its potential as an effective drug for pain management.

Nicotinic ligands targeting relevant CNS receptors can induce analgesia by an opiate-independent mechanism with a potency much greater than that of morphine.

Metanicotine has been reported to possess high selectivity for central nicotinic receptor subtypes, as compared to peripheral ganglionic and muscular nicotinic receptors, and to elicit a dose dependent antinociceptive effect in animal studies. JPET, 279: 1422–29 (1996). See also Damaj et al. Society for Neuroscience Abstracts, Vol. 23, Pt. 1, No. 266.9 (1997).

Metanicotine has also been shown to exhibit therapeutic efficacy in the treatment of central nervous system (CNS) disorders, such as senile dementia of the Alzheimer's type and Parkinson's disease, and of inflammatory bowel disease, e.g., ulcerative colitis. See, for example, U.S. Pat. Nos. 5,212,188, 5,616,716 and 5,604,231. The entire disclosures of these three (3) patents are incorporated by reference in the present specification, as though set forth herein in full.

Insofar as is known, the use of metanicotine and structurally analogous compounds for the treatment of female-specific and/or chronic pain has not been reported previously.

SUMMARY OF THE INVENTION

The present invention provides a method for treating female-specific and or chronic pain. The method of the invention involves administering to a female patient in need of such treatment a therapeutically effective amount of a compound having the formula:

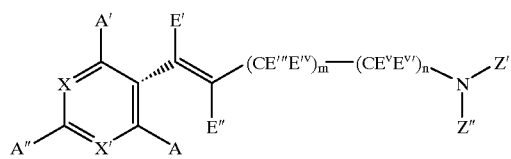

(I)

wherein each of X and X' are independently selected from nitrogen or carbon bonded to a substituent species characterized as having a sigma m value greater than 0, often greater than 0.1, and generally greater than 0.2, and even greater than 0.3; less than 0 and generally less than −0.1; or 0; as determined in accordance with Hansch et al., Chem. Rev. 91:165 (1991); m is an integer and n is an integer such that the sum or m plus n is 1, 2, 3, 4, 5, 6, 7, or 8, preferably 1, 2, or 3, and most preferably is 2 or 3; the wavy line in the structure indicates that the compound can have the cis (Z) or trans (E) from; $E^I$, $E^{II}$, $E^{III}$, $E^{IV}$, $E^V$ and $E^{VI}$ are hydrogen, or straight chain or branched alkyl including $C_1$–$C_8$, preferably $C_1$–$C_5$, (such as methyl, ethyl, or isopropyl) or halo substituted straight chain or branched alkyl including $C_1$–$C_8$, preferably $C_1$–$C_5$, (such as triflouromethyl or trichloromethyl) and at least one of $E^I$, $E^{II}$, $E^{III}$, $E^{IV}$, $E^V$, and $E^{VI}$ is non-hydrogen and the remaining $E^I$, $E^{II}$, $E^{III}$, $E^{IV}$, $E^V$, and $E^{VI}$ are hydrogen, preferably $E^I$, $E^{II}$, $E^{III}$, $E^{IV}$, $E^V$, and $E^{VI}$ are hydrogen; and Z' and Z" are hydrogen or straight chain or branched alkyl including $C_1$–$C_8$, preferably $C_1$–$C_5$, (such as methyl, ethyl, or isopropyl) and preferably at least one of Z' and Z" is hydrogen, and most preferably Z' is hydrogen and Z" is methyl; alternatively Z' is hydrogen and Z" represents an unsubstituted or substituted cycloaliphatic or aromatic ring structure selected from the group of cyclopropyl, cyclobutyl, cyclopentyl, cyclohexyl, cycloheptyl, adamantyl, quinuclidinyl, pyridyl, quinolinly, pyrimidinyl, phenyl, or benzyl; the cycloaliphatic or aromatic ring structure substituents being at least one selected from the group of alkyl, including $C_1$–$C_8$, halo or amino substituents; alternatively Z' and Z", and the associated nitrogen atom can form a ring structure such as aziridinyl, azetidinyl, pyrollidinyl, piperidinyl, quinuclidinyl, piperazinyl, or morpholinyl.

More specifically, X and X' include N, C—H, C—F, C—Cl, C—Br, C—I, C—R', C—NR'R418 , C—CF$_3$, C—OH, C—CN, C—NO$_2$, C—C$_2$R', C—SH, C—SCH$_3$, C—N$_3$, C—SO$_2$CH$_3$, C—OR', C—SR', C—C(=O)NR'R", C—NR", C(=O)R', C—C(=O)R', C—C(=O)OR', C(CH$_2$)$_q$OR', C—OC(=O)R', COC(=O)NR'R" and C—NR'C(=O)OR' where R' and R" are individually hydrogen or lower alkyl (e.g., $C_1$–$C_{10}$ alkyl, preferably $C_1$–$C_5$ alkyl, and more preferably methyl, ethyl, isopropyl or isobutyl), an unsubstituted or substituted aromatic group-containing species and q is an integer from 1 to 6. R' and R" can be straight chain or branched alkyl, or R' and R" can form a cycloalkyl moiety (e.g., cyclopropyl cyclobutyl, cyclopentyl, cyclohexyl, cycloheptyl, adamantyl, and quinuclidinyl). Representative aromatic group-containing species include pyridyl, quinolinyl, pyrimidinyl, phenyl, and benzyl (where any of the foregoing can be suitably substituted with at least one substituent group, such as alkyl, halo, or amino substituents). Other representative aromatic ring systems are set forth in Gibson et al., *J. Med. Chem.* 39:4065 (1996). When X and X' represent a carbon atom bonded to a substituent species, that substituent species often has a sigma m value which is between about −0.3 and about 0.75, and frequently between about −0.25 and about 0.6. In certain circumstances the substituent species is characterized as having a sigma m value not equal to 0.

A, A' and A" individually represent those species described as substituent species to the aromatic carbon atom previously described for X and X'; and usually include hydrogen, halo (e.g., F', Cl, Br, or I), alkyl (e.g., lower straight chain or branched $C_{1-8}$ alkyl, but preferably methyl or ethyl), or NX"X'" where X" and X'" are individually hydrogen or lower alkyl, including $C_1$–$C_8$, preferably $C_1$–$C_5$ alkyl. In addition, it is highly preferred that A is hydrogen, it is preferred that A' is hydrogen, and normally A" is hydrogen. Generally, both A and A' are hydrogen; sometimes A and A' are hydrogen, and A" is amino, methyl or ethyl; and often A, A' and A" are all hydrogen. In a preferred embodiment, m is 1 or 2, n is 1, $E^I$, $E^{II}$, $E^{III}$, $E^{IV}$ and $E^{IV}$ each are hydrogen, and $E^V$ is alkyl (e.g., methyl). Depending upon the identity and positioning of each individual $E^I$, $E^{II}$, $E^{III}$, $E^{IV}$, $E^V$ and $E^{VI}$, certain compounds can be optically active. Additionally, compounds of the present invention can have chiral centers within the alkenyl side chain e.g., the compound can have an R or S configuration depending on the selection of $E^{III}$, $E^{IV}$, $E^V$ and $E^{VI}$, with the S configuration being preferred. Depending upon $E^I$, $E^{II}$, $E^{III}$, $E^{IV}$, $E^V$ and $E^{VI}$, compounds of the present invention have chiral centers, and the present invention relates to racemic mixtures of such compounds as well substantially enamiomerically pure compounds. Typically, the selection of m, n, $E^I$, $E^{II}$, $E^{III}$, $E^{IV}$, $E^V$ and $E^{VI}$ is such that up to about 4, and frequently up to 3, and usually 1 or 2, of the substituents designated as $E^I$, $E^{II}$, $E^V$ and $E_{VI}$ are non-hydrogen substituents (i.e., substituents such as lower alkyl or halo-substituted lower alkyl). Typically, X is CH, CBr or COR. Most preferably, X' is nitrogen.

The method of the invention alleviates female-specific pain, without producing appreciable activity of peripheral ganglionic and muscular sites, thereby minimizing adverse cardiorespiratory side effects, such as increased blood pressure and heart rate.

The method of the invention may also be used to advantage for treating chronic pain, again without producing appreciable side effects.

Preferably, the method of the invention is performed by administering a therapeutically effective amount of a compound having the structural formula (I), above, wherein X is nitrogen or carbon bonded to a substituent species characterized as having a sigma m value greater than 0 or less than 0; X' is nitrogen; A, A' and A" individually represent substituent species characterized as having a sigma m value greater than 0, less than 0, or 0; m is an integer and n is an integer such that the sum of m plus n is 1, 2, 3, 4, 5, 6, 7, or 8; $E^I$, $E^{II}$, $E^{III}$, $E^{IV}$, $E^V$ and $E^{VI}$ individually represent hydrogen, lower alkyl, including $C_1$–$C_8$, or halo substituted lower alkyl, including $C_1$–$C_8$; and Z and Z" individually represent hydrogen or lower alkyl.

More preferably, the method of the invention involves administration of a compound of structural formula (I) wherein Z' is hydrogen or methyl and Z" is hydrogen; E' and E" are each hydrogen; X' is nitrogen; $E^{III}$, $E^{IV}$ and $E^V$ are hydrogen and $E^{VI}$ is hydrogen or methyl; A, A' and A" are each hydrogen and m+n=2 or 3 and pharmaceutically acceptable salts thereof.

DETAILED DESCRIPTION OF THE INVENTION

Compounds for use in the methods of the present invention, including their pharmaceutically acceptable salts, have the formula:

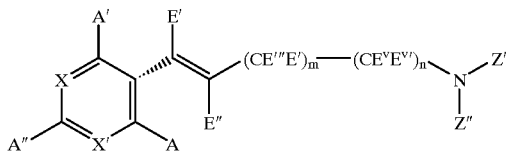

where each of X and X' are independently selected from nitrogen or carbon bonded to a substituent species characterized as having a sigma m value greater than 0, often greater than 0.1, and generally greater than 0.2, and even greater than 0.3; less than 0 and generally less than –0.1; or 0; as determined in accordance with Hansch et al., Chem. Rev. 91:165 (1991); m is an integer and n is an integer such that the sum of m plus n is 1, 2, 3, 4, 5, 6, 7, or 8, preferably 1, 2, or 3, and most preferably is 2 or 3; the wavy line in the structure indicates that the compound can have the cis (Z) or trans (E) form; $E^I$, $E^{II}$, $E^{III}$, $E^{IV}$, $E^V$ and $E^{VI}$ are hydrogen, or straight chain or branched alkyl including $C_1$–$C_8$, preferably $C_1$–$C_5$, (such as methyl, ethyl, or isopropyl) or halo substituted straight chain or branched alkyl having $C_1$–$C_8$, preferably $C_1$–$C_5$, (such as triflouromethyl or trichloromethyl) and at least one of $E^I$, $E^{II}$, $E^{III}$, $E^{IV}$, $E^V$, and $E^{VI}$ is non-hydrogen and the remaining $E^I$, $E^{II}$, $E^{III}$, $E^{IV}$, $E^V$, and $E^{VI}$ are hydrogen, preferably $E^I$, $E^{II}$, $E^{III}$, $E^{IV}$, $E^V$, and $E^{VI}$ are hydrogen; and Z' and Z" are hydrogen or straight chain or branched alkyl including $C_1$–$C_8$, preferably $C_1$–$C_5$, (such as methyl, ethyl, or isopropyl) and preferably at least one of Z' and Z" is hydrogen, and most preferably Z' is hydrogen and Z" is methyl; alternatively Z' is hydrogen and Z" represents an unsubstituted or substituted cycloaliphatic or aromatic ring structure selected from the group of cyclopropyl, cyclobutyl, cyclopentyl, cyclohexyl, cycloheptyl, adamantyl, quinuclidinyl, pyridyl, quinolinly, pyrimidinyl, phenyl, or benzyl; the cycloaliphatic or aromatic ring structure substituents being at least one selected from the group of alkyl, including $C_1$–$C_8$ halo or amino substituents; alternatively Z' and Z", and the associated nitrogen atom can form a ring structure such as aziridinyl, azetidinyl, pyrollidinyl, piperidinyl, quinuclidinyl, piperazinyl, or morpholinyl.

More specifically, X and X' include N, C—H, C—F, C—Cl, C—Br, C—I, C—R', C—NR'R", C—CF$_3$, C—OH, C—CN, C—NO$_2$, C—C$_2$', C—SH, C—SCH$_3$, C—N$_3$, C—SO$_2$CH$_3$, C—OR', C—SR', C—C(=O)NR'R", C—NR'C(=O)R', C—C(=O)R', C—C(=O)OR', C(CH$_2$)$_q$OR', C—OC(=O)R', COC(=O)NR'R" and C—NR'C (=O)OR' where R' and R" are individually hydrogen or lower alkyl (e.g., $C_1$–$C_{10}$ alkyl, preferably $C_1$–$C_5$ alkyl, and more preferably methyl, ethyl, isopropyl or isobutyl), an unsubstituted or substituted aromatic group- containing species and q is an integer from 1 to 6. R' and R" can be straight chain or branched alkyl, or R' and R" can form a cycloalkyl moiety (e.g., cyclopropyl cyclobutyl, cyclopentyl, cyclohexyl, cycloheptyl, adamantyl, and quinuclidinyl). Representative aromatic group-containing species include pyridyl, quinolinyl, pyrimidinyl, phenyl, and benzyl (where any of the foregoing can be suitably substituted with at least one substituent group, such as alkyl, halo, or amino substituents). Other representative aromatic ring systems are set forth in Gibson et al., *J. Med. Chem.* 39:4065 (1996). When X and X' represent a carbon atom bonded to a substituent species, that substituent species often has a sigma m value which is between about –0.3 and about 0.75, and frequently between about –0.25 and about 0.6. In certain circumstances, the substituent species is characterized as having a sigma m value not equal to 0.

A, A' and A" individually represent those species described as substituent species to the aromatic carbon atom previously described for X and X'; and usually include hydrogen, halo (e.g., F, Cl, Br, or I), alkyl (e.g., lower straight chain or branched $C_{1-8}$ alkyl, but preferably methyl or ethyl), or NX"X'" where X" and X'" are individually hydrogen or lower alkyl, including $C_1$–$C_8$, preferably $C_1$–$C_5$ alkyl. In addition, it is highly preferred that A is hydrogen, it is preferred that A' is hydrogen, and normally A" is hydrogen. Generally, both A and A' are hydrogen; sometimes A and A' are hydrogen, and A" is amino, methyl or ethyl; and often A, A' and A" are all hydrogen. In a preferred embodiment, m is 1 or 2, n is 1, $E^I$, $E^{II}$, $E^{III}$, $E^{IV}$ and $E^{VI}$ each are hydrogen, and $E^V$ is alkyl (e.g., methyl). Depending upon the identity and positioning of each individual $E^I$, $E^{II}$, $E^{III}$, $E^{IV}$, $E^V$ and $E^{VI}$, certain compounds can be optically active. Additionally, compounds of the present invention can have chiral centers within the alkenyl side chain e.g., the compound can have an R or S configuration depending on the selection of $E^{III}$, $E^{IV}$, $E^V$ and $E^{VI}$, with the S configuration being preferred. Depending upon $E^I$, $E^{II}$, $E^{III}$, $E^{IV}$, $E^V$ and $E^{VI}$, compounds of the present invention have chiral centers, and the present invention includes racemic mixtures of such compounds as well substantially enantiomerically pure compounds. Typically, the selection of m, n, $E^I$, $E^{II}$, $E^{III}$, $E^{IV}$, $E^V$ and $E^{VI}$ is such that up to about 4, and frequently up to 3, and usually 1 or 2, of the substituents designated as $E^I$, $E^{II}$, $E^{III}$, $E^{IV}$, $E^V$ and $E^{VI}$ are non-hydrogen substituents (i.e., substituents such as lower alkyl or halo-substituted lower alkyl). Typically, X is CH, CBr or COR. Most preferably, X' is nitrogen.

A preferred group of compounds for use in the method of the invention are those having structural formula (I), above, wherein X is nitrogen or carbon bonded to a substituent species characterized as having a sigma m value greater than 0 or less than 0; X' is nitrogen; A, A' and A" individually represent substituent species characterized as having a sigma m value greater than 0, less than 0, or 0; m is an integer and n is an integer such that the sum of m plus n is 1, 2, 3, 4, 5, 6, 7, or 8; $E^I$, $E^{II}$, $E^{III}$, $E^{IV}$, $E^V$ and $E^{VI}$ individually represent hydrogen, lower alkyl, or halo substituted lower alkyl; and Z and Z" individually represent hydrogen or lower alkyl.

Another preferred group of compounds includes those of structural formula I, above, wherein the compound is in its E or Z form; Z' is hydrogen or methyl and Z" is hydrogen; E' and E" are each hydrogen; X' is nitrogen; $E^{III}$, $E^{IV}$ and $E^V$ are hydrogen and $E^{VI}$ is hydrogen or methyl; A' and A" are each hydrogen and m+n=2 or 3 and pharmaceutically acceptable salts thereof.

Of particular interest are compounds of the formula:

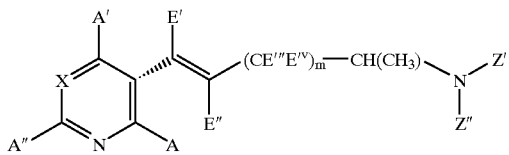

where m, $E^I$, $E^{II}$, $E^{III}$, $E^{IV}$, X, Z', Z", A, A' and A" are as defined hereinbefore.

Representative compounds include (4E)-N-methyl-5-(3-pyridyl)-4-penten-2-amine, (4E)-N-methyl-5-(5-pyrimidinyl)-4-penten-2-amine, (4E)-N-methyl-5-(5-1S methoxy-3-pyridyl)-4-penten-2-amine, (4E)-N-methyl-5-(6-amino-5-methyl-3-pyridyl)-4-penten-2-amine, (2R)-(4E)-N-methyl-5-(3-pyridyl)-4-penten-2-amine, (2R)-(4E)-N-methyl-5-(5-isopropoxy-3-pyridyl)-4-penten-2-amine, (4E)-N-methyl-S-(5-bromo-3-pyridyl)-4-penten-2-amine, (4E)-N-methyl-S-(5-ethoxy-3-pyridyl)-4-penten-2-amine, (2S)-(4E)-N-methyl-5-(3-pyridyl)-4-penten-2-amine, (4E)-N-methyl-5-(5-isopropoxy-3-pyridyl)-4-penten-2-amine and (2S)-(4E)-N-methyl-S-(5-isopropoxy-3-pyridyl)-4-penten-2-amine.

Other representative compounds are (3E) and (3Z)-N-methyl-4-(3-pyridyl)-2-methyl-3-buten-1-amine, (3E) and (3Z)-N-methyl-4-(3-pyridyl)-3-methyl-3-buten-1-amine, (5E) and (5Z)-N-methyl-6-(3-pyridyl)-5-hexen-3-amine, (4E) and (4Z)-N-methyl-5-(3-pyridyl)-2-methyl-4-penten-2-amine, (4E) and (4Z)-N-methyl-5-(3-pyridyl)-3-methyl-4-penten-2-amine, (4E) and (4Z)-N-methyl-5-(3-pyridyl)-4-penten-2-amine, (4E) and (4Z)-N-methyl-5-(3-pyridyl)-1,1,1-trifluoro-4-penten-2-amine, (4E) and (4Z)-N-methyl-5-(3-pyridyl)-4-methyl-4-penten-1-amine, (4E) and (4Z)-N-methyl-5-(3-pyridyl)-4-methyl-4-penten-2-amine, (1E) and (1Z)-N-methyl-1-(3-pyridyl)-1-octen-4-amine, (1E) and (1Z)-N-methyl-1-(3-pyridyl)-5-methyl-1-hepten-4-amine, (5E) and (5Z)-N-methyl-6-(3-pyridyl)-5-methyl-5-hexen-2-amine, (5E) and (5Z)-N-methyl-6-(3-pyridyl)-5-hexen-2-amine, (5E) and (5Z)-N-methyl-6-(3-pyridyl)-5-methyl-5-hexen-3-amine, (3E) and (3Z)-4-(3-pyridyl)-2-methyl-3-buten-1-amine, (3E) and (3Z)-4-(3-pyridyl)-3-methyl-3-buten-1-amine, (5E) and (5Z)-6-(3-pyridyl)-5-hexen-3-amine, (4E) and (4Z)-5-(3-pyridyl)-2-methyl-4-penten-2-amine, (4E) and (4Z)-5-(3-pyridyl)-3-methyl-4-penten-2-amine, (4E) and (4Z)-5-(3-pyridyl)-4-penten-2-amine, (4E) and (4Z)-5-(3-pyridyl)-1,1,1-trifluoro-4-penten-2-amine, (4E) and (4Z)-5-(3-pyridyl)-4-methyl-4-penten-1-amine, (4E) and (4Z)-5-(3-pyridyl)-4-methyl-4-penten-2-amine, (1E) and (1Z)-1-(3-pyridyl)-1-octen-4-amine, (5E) and (5Z)-6-(3-pyridyl)-5-methyl-5-hexen-2-amine, (5E) and (5Z)-6-(3-pyridyl)-5-hexen-2-amine, and (5E) and (5Z)-6-(3-pyridyl)-5-methyl-5-hexen-3-amine. See, U.S. Pat. No. 5,616,716 to Dull et al.

Other representative compounds are set forth in U.S. Pat. No. 5,212,188 to Caldwell et al., U.S. Pat. No. 5,616,707 to Crooks et al., U.S. Pat. No. 5,663,356 to Reucroft et al., U.S. Pat. No. 5,811,442 to Bencherif et al., and U.S. Pat. No. 5,861,423 to Caldwell et al.

The term "metanicotine" as used herein includes both the cis(Z) and trans(E) isomeric forms thereof; however, the trans(E) form is preferred for use in practicing the method of the invention. (E)-metanicotine-type compounds can be prepared using the techniques set forth by Löffler et al., Chem, Ber., 42, pp. 3431–3438 (1909) and Laforge, J.A.C.S., 50, p. 2477 (1928) from substituted nicotine-type compounds. Certain 6-substituted metanicotine-type compounds can be prepared from the corresponding 6-substituted nicotine-type compounds using the general methods of Acheson et al., J. Chem. Soc., Perkin Trans. 1, 2, pp. 579–585 (1980). The requisite precursors for such compounds, 6-substituted nicotine-type compounds, can be synthesized from 6-substituted nicotinic acid esters using the general methods disclosed by Rondahl, Acta Pharm. Suec., 14, pp 113–118 (1977). Preparation of certain 5-substituted metanicotine-type compounds can be accomplished from the corresponding 5-substituted nicotine-type compounds using the general method taught by Acheson et al., J. Chem. Soc., Perkin Trans. 1, 2, pp. 579–585 (1980). The 5-halo-substituted nicotine-type compounds (e.g., fluoro- and bromo-substituted nicotine-type compounds) and the 5-amino nicotine-type compounds can be prepared using the general procedures disclosed by Rondahl, Act. Pharm. Suec., 14, pp. 113–118 (1977). The 5-trifluoromethyl nicotine-type compounds can be prepared using the techniques and materials set forth in Ashimori et al., Chem. Pharm. Bull., 38(9), pp. 2446–2458 (1990) and Rondahl, Acta Pharm. Suec., 14, pp.113–118 (1977).

Furthermore, preparation of certain metanicotine-type compounds can be accomplished using a palladium catalyzed coupling reaction of an aromatic halide and a terminal olefin containing a protected amine substituent, removal of the protective group to obtain a primary amine, and optional alkylation to provide a secondary or tertiary amine. In particular, certain metanicotine-type compounds can be prepared by subjecting a 3-halo-substituted, 5-substituted pyridine compound or a 5-halo-substituted pyrimidine compound to a palladium catalyzed coupling reaction using an olefin possessing a protected amine functionality (e.g., such an olefin provided by the reaction of a phthalimide salt with 3-halo-1-propene, 4-halo-1-butene, 5-halo-1-pentene or 6-halo-1-hexene). See, Frank et al., J. Org. Chem., 43(15), pp. 2947–2949 (1978) and Malek et al., J. Org. Chem., 47, pp. 5395–5397 (1982). Alternatively, certain metanicotine-type compounds can be prepared by coupling an N-protected, modified amino acid residue, such as 4-(N-methyl-N-tert-butyloxycarbonyl)aminobutyric acid methyl ester, with an aryl lithium compound, as can be derived from a suitable aryl halide and butyl lithium. The resulting N-protected aryl ketone is then chemically reduced to the corresponding alcohol, converted to the alkyl halide, and subsequently dehydrohalogenated to introduce the olefin functionality. Removal of the N-protecting group then affords the desired metanicotine-type compound.

There are a number of different methods for providing (Z)-metanicotine-type compounds. In one method, (Z)-metanicotine-type compounds can be synthesized from nicotine-type compounds as a mixture of E and Z isomers; and the (Z)-metanicotine-type compounds can then be separated by chromatography using the types of techniques disclosed by Sprouse et al., Abstracts of Papers, p. 32, *Coresta/TCRC Joint Conference* (1972). In another method, metanicotine-type compounds can be prepared by the controlled hydrogenation of the corresponding acetylenic compound (e.g., an N-methyl-4-(3-pyridinyl)-3-butyn-1-amine type compound). For example, certain 5-substituted (Z)-metanicotine-type compounds and certain 6-substituted (Z)-metanicotine-type compounds can be prepared from 5-substituted-3-pyridinecarboxaldehydes and 6-substituted-3-pyridinecarboxaldehydes, respectively. Representative synthetic techniques for (Z)-metanicotine-type compounds are set forth in U.S. Pat. No. 5,597,919 to Dull et al.

There are a number of methods by which the (Z)-olefinic isomers of aryl substituted olefinic amine compounds can be synthetically produced. In one approach, the (Z)-isomers of aryl substituted olefinic amine compounds can be prepared by the controlled hydrogenation of the corresponding alkynyl compounds (e.g., a N-methyl-5-(3-pyridyl)-4-butyn-2-amine-type compound) using commercially available Lindlar catalyst (Aldrich Chemical Company) using the methodology set forth in H. Lindlar et al., *Org. Syn.* 46: 89 (1966). The requisite alkynyl compounds can be prepared by the palladium catalyzed coupling of an aromatic halide, preferably a 3-bromopyridine-type or a 3-iodopyridine-type compound with an alkynyl side chain compound (e.g., an N-methyl-4-pentyn-2-amine-type compound). Typically the methodolgy set forth in L. Bleicher et al., *Synlett.* 1115 (1995) is used for the palladium catalyzed coupling of an aryl halide with a monosubstituted alkyne in the presence of copper(I) iodide and triphenylphosphine and potassium carbonate as a base. Alkynyl compounds such as N- methyl-4-pentyn-2-amine can be prepared from commercially available 4-pentyn-2-ol (Aldrich Chemical Company) by treatment with p-toluenesulfonyl chloride in pyridine, followed by reaction of the resulting 4-pentyn-2-ol p-toluenesulfonate with excess methylamine either as a 40% aqueous solution or as a 2.0 M solution in tetrahydrofuran. In some instances it may be necessary to protect the amino functionality of the N-methyl-4-pentyn-2-amine-type compound by treatment with di-tert-butyl dicarbonate to give the tert-butoxycarbonyl protected amine-type compound. Such protected amine compounds may undergo the palladium catalyzed coupling with aryl halides and the subsequent controlled hydrogenation of the resulting alkynyl compound more easily than the unprotected amine compounds. The tert-butoxycarbonyl protecting group can be easily removed using a strong acid such as trifluoroacetic acid to yield the (Z)-olefinic isomers of aryl substituted olefinic amine compounds.

The methods by which aryl substituted olefinic amine compounds of the present invention can be synthetically produced can vary. An olefinic alcohol, such as 4-penten-2-ol, is condensed with an aromatic halide, such as 3-bromopyridine or 3-iodopyridine. Typically, the types of procedures set forth in Frank et al., *J. Org. Chem.,* 43, pp. 2947–2949 (1978) and Malek et al., *J. Org. Chem.,* 47, pp. 5395–5397 (1982) involving a palladium-catalyzed coupling of an olefin and an aromatic halide are used. The olefinic alcohol optionally can be protected as a t-butyldimethylsilyl ether prior to the coupling. Desilylation then produces the olefinic alcohol. The alcohol condensation product then is converted to an amine using the type of procedures set forth in deCosta et al., *J. Org. Chem.,* 35, pp. 4334–4343 (1992). Typically, the alcohol condensation product is converted to the aryl substituted olefinic amine by activation of the alcohol using methanesulfonyl chloride or p-toluenesulfonyl chloride, followed by mesylate or tosylate displacement using ammonia, or a primary or secondary amine. Thus, when the amine is ammonia, an aryl substituted olefinic primary amine compound is provided; when the amine is a primary amine such as methylamine or cyclobutylamine, an aryl substituted olefinic secondary amine compound is provided; and when the amine is a secondary amine such as dimethylamine or pyrrolidine, an aryl substituted olefinic tertiary amine compound is provided. Other representative olefinic alcohols include 4-penten-1-ol, 5-hexen-2-ol, 5-hexen-3-ol, 3-methyl-3-buten-1-ol, 2-methyl-3-buten-1-ol, 4-methyl-4-penten-1-ol, 4-methyl-4-penten-2-ol, 1-octen-4-ol, 5-methyl-1-hepten-4-ol, 4-methyl-5-hexen-2-ol, 5-methyl-5-hexen-2-ol, 5-hexen-2-ol and 5-methyl-5-hexen-3-ol. Trifluormethyl- substituted olefinic alcohols, such as 1,1,1 -trifluoro-4-penten-2-ol, can be prepared from 1-ethoxy-2,2,2-trifluoro-ethanol and allyl-trimethylsilane using the procedures of Kubota et al., *Tetrahedron Letters, Vol.* 33(10), pp. 1351–1354 (1992), or from trifluoroacetic acid ethyl ester and allyltributylstannane using the procedures of Ishihara et al., *Tetrahedron Letters, Vol.* 34(56), pp. 5777–5780 (1993). Certain olefinic alcohols are optically active, and can be used as enantiomeric mixtures or as pure enantiomers in order to provide the corresponding optically active forms of aryl substituted olefinic amine compounds. When an olefinic allylic alcohol, such as methallyl alcohol, is reacted with an aromatic halide, an aryl substituted olefinic aldehyde is produced; and the resulting aldehyde can be converted to an aryl substituted olefinic amine compound by reductive amination (e.g., by treatment using an alkyl amine and sodium cyanoborohydride). Preferred aromatic halides are 3-bromopyridine-type compounds and 3-iodopyridine-type compounds. Typically, substituent groups of such 3-halopyridine-type compounds are such that those groups can survive contact with those chemicals (e.g., tosylchloride and methylamine) and the reaction conditions experienced during the preparation of the aryl substituted olefinic amine compound. Alternatively, substituents such as —OH, —NH$_2$ and —SH can be protected as corresponding acyl compounds, or substituents such as —NH$_2$ can be protected as a phthalimide functionality.

The manner in which certain aryl substituted olefinic amine compounds possessing a branched side chain, such as (4E)-N-methyl-5-(5-isopropoxy-3 -pyridyl)-4-penten-2-amine, are provided can vary. By using one synthetic approach, the latter compound can be synthesized in a convenient manner, in which the side chain, N-methyl-N-(tert-butoxycarbonyl)-4-penten-2-amine is coupled with the 3-substituted 5-halo-substituted pyridine, 5-bromo-3-isopropoxypyridine, under Heck reaction conditions, followed by removal of the tert-butoxycarbonyl protecting group. Typically, the types of procedures set forth in W. C. Frank et al., *J. Org. Chem.* 43: 2947 (1978) and N. J. Malek et al., *J. Org. Chem.* 47: 5395 (1982) involving a palladium-catalyzed coupling of an olefin and an aromatic halide are used. The required N-methyl-N-(tert-butoxycarbonyl)-4-penten-2-amine can be synthesized as follows: (i) Commercially available 4-penten-2-ol (Aldrich Chemical Company, Lancaster Synthesis Inc.) can be treated with p-toluenesulfonyl chloride in pyridine to yield 4-penten-2-ol p-toluenesulfonate, previously described by T. Michel, et al., *Liebigs Ann.* 11: 1811 (1996). (ii) The resulting tosylate can be heated with 20 molar equivalents of methylamine as a 40% aqueous solution to yield N-methyl-4-penten-2-amine. (iii) The resulting amine, such as previously mentioned by A. Viola et al., *J. Chem. Soc., Chem. Commun.* (21): 1429

(1984), can be allowed to react with 1.2 molar equivalents of di-tert-butyl dicarbonate in dry tetrahydrofuran to yield the side chain, N-methyl-N-(tert-butoxycarbonyl)-4-penten-2-amine. The halo-substituted pyridine, (e.g., 5-bromo-3-isopropoxypyridine) can be synthesized by two different routes. In one preparation, 3,5-dibromopyridine is heated at 140° C. for 14 hours with 2 molar equivalents of potassium isopropoxide in dry isopropanol in the presence of copper powder (5%, w/w of the 3,5-dibromopyridine) in a sealed glass tube to yield 5-bromo-3-isopropoxypyridine. A second preparation of 5-bromo-3-isopropoxypyridine from 5-bromonicotinic acid can be performed as follows: (i) 5-Bromonicotinic acid is converted to 5-bromonicotinamide by treatment with thionyl chloride, followed by reaction of the intermediate acid chloride with aqueous ammonia. (ii) The resulting 5-bromonicotinamide, previously described by C. V. Greco et al., *J. Heterocyclic Chem.* 7(4): 761 (1970), is subjected to Hofmann degradation by treatment with sodium hydroxide and a 70% solution of calcium hypochlorite. (iii) The resulting 3-amino-5-bromopyridine, previously described by C. V. Greco et al., *J. Heterocyclic Chem.* 7(4): 761 (1970), can be converted to 5-bromo-3-isopropoxypyridine by diazotization with isoamyl nitrite under acidic conditions, followed by treatment of the intermediate diazonium salt with isopropanol to yield 5-bromo-3-isopropoxypyridine. The palladium-catalyzed coupling of 5-bromo-3-isopropoxypyridine and N-methyl-N-(tert-butoxycarbonyl)-4-penten-2-amine is carried out in acetonitrile-triethylamine (2:1, v,v) using a catalyst consisting of 1 mole % palladium(II) acetate and 4 mole % tri-o-tolylphosphine. The reaction can be carried out by heating the components at 80° C. for 20 hours to yield (4E)-N-methyl-N-(tert-butoxycarbonyl)-5-(5-isopropoxy-3-pyridyl)-4-penten-2-amine. Removal of the tert-butoxycarbonyl protecting group can be accomplished by treatment with 30 molar equivalents of trifluoroacetic acid in anisole at 0° C. to afford (4E)-N-methyl-5-(5-isopropoxy-3-pyridyl)-4-penten-2-amine.

The manner in which certain aryl substituted olefinic amine compounds possessing a branched side chain are provided can vary. Using one synthetic approach, a compound such as (4E)-N-methyl-5-(5-methoxy-3-pyridyl)-4-penten-2-amine can be synthesized by coupling a halo-substituted pyridine, 5-bromo-3-methoxypyridine with an olefin containing a secondary alcohol functionality, 4-penten-2-ol, under Heck reaction conditions; and the resulting pyridyl alcohol intermediate can be converted to its p-toluenesulfonate ester, followed by treatment with methylamine. Typically, the types of procedures set forth in W. C. Frank et al., *J. Org. Chem.* 43: 2947 (1978) and N. J. Malek et al., *J. Org. Chem.* 47: 5395 (1982) involving a palladium-catalyzed coupling of an olefin and an aromatic halide are used. The required halo-substituted pyridine, 5-bromo-3-methoxypyridine is synthesized using methodology similar to that described by H. J. den Hertog et al., *Recl. Trav. Chim. Pays-Bas* 74:1171 (1955), namely by heating 3,5-dibromopyridine with 2.5 molar equivalents of sodium methoxide in dry methanol in the presence of copper powder (5%, w/w of the 3,5-dibromopyridine) in a sealed glass tube at 1500 for 14 hours to produce 5-bromo-3-methoxypyridine. The resulting 5-bromo-3-methoxypyridine, previously described by D. L. Comins, et al., *J. Org. Chem.* 55: 69 (1990), can be coupled with 4-penten-2-ol in acetonitrile-triethylamine (1.1:1, v/v) using a catalyst consisting of 1 mole % palladium(II) acetate and 4 mole % tri-o-tolylphosphine. The reaction is carried out by heating the components in a sealed glass tube at 140° C. for 14 hours to yield (4E)-N-methyl-5-(5-methoxy-3-pyridyl)-4-penten-2-ol. The resulting alcohol is treated with 2 molar equivalents of p-toluenesulfonyl chloride in dry pyridine at 0° C. to produce (4E)-N-methyl-5-(5-methoxy-3-pyridyl)-4-penten-2-ol p-toluensulfonate. The tosylate intermediate is treated with 120-molar equivalents of methylamine as a 40% aqueous solution, containing a small amount of ethanol as a co-solvent to produce (4E)-N-methyl-S-(5-methoxy-3-pyridyl)-4-penten-2-amine.

The manner in which optically active forms of certain aryl substituted olefinic amine compounds, such as (2S)-(4E)-N-methyl-5-(3-pyridyl)-4-penten-2-amine, are provided can vary. In one synthetic approach, the latter type of compound is synthesized by coupling a halo-substituted pyridine, 3-bromopyridine, with an olefin possessing a chiral, secondary alcohol functionality, (2R)-4-penten-2-ol, under Heck reaction conditions. The resulting chiral pyridyl alcohol intermediate, (2R)-(4E)-5-(3-pyridyl)-4-penten-2-ol is converted to its corresponding p-toluenesulfonate ester, which is subsequently treated with methylamine, resulting in tosylate displacement with inversion of configuration. Typically, the types of procedures set forth in W. C. Frank et al., *J. Org. Chem.* 43: 2947 (1978) and N. J. Malek et al., *J. Org. Chem.* 47: 5395 (1982) involving a palladium-catalyzed coupling of an aromatic halide and an olefin are used. The chiral side chain, (2R)-4-penten-2-ol can be prepared by treatment of the chiral epoxide, (R)-(+)-propylene oxide (commercially available from Fluka Chemical Company) with vinylmagnesium bromide in tetrahydrofuran at low temperatures (−25 to −10° C.) using the general synthetic methodology of A. Kalivretenos, J. K. Stille, and L. S. Hegedus, *J. Org. Chem.* 56: 2883 (1991), to afford (2R)-4-penten-2-ol. The resulting chiral alcohol is subjected to a Heck reaction with 3-bromopyridine in acetonitrile-triethylamine (1:1, v/v) using a catalyst consisting of 1 mole % palladium(II) acetate and 4 mole % tri-o-tolylphosphine. The reaction is done by heating the components at 140° C. for 14 hours in a sealed glass tube, to produce the Heck reaction product, (2R)-(4E)-5-(3-pyridyl)-4-penten-2-ol. The resulting chiral pyridyl alcohol is treated with 3 molar equivalents of p-toluenesulfonyl chloride in dry pyridine at 0° C., to afford the tosylate intermediate. The p-toluenesulfonate ester is heated with 82 molar equivalents of methylamine as a 40% aqueous solution, containing a small amount of ethanol as a co-solvent, to produce (2S)-(4E)-N-methyl-5-(3-pyridyl)-4-penten-2-amine. In a similar manner, the corresponding aryl substituted olefinic amine enantiomer, such as (2R)-(4E)-N-methyl-5-(3-pyridyl)-4-penten-2-amine, can be synthesized by the Heck coupling of 3-bromopyridine and (2S)-4-penten-2-ol. The resulting intermediate, (2S)-(4E)-5-(3-pyridyl)-4-penten-2-ol, is converted to its p-toluenesulfonate, which is subjected to methylamine displacement. The chiral alcohol, (2S)-4-penten-2-ol, is prepared from (S)-(−)-propylene oxide (commercially available from Aldrich Chemical Company) using a procedure analogous to that described for the preparation of (2R)-4-penten-2-ol from (R)-(+)-propylene oxide as reported by A. Kalivretenos, J. K. Stille, and L. S. Hegedus, *J. Org. Chem.* 56: 2883 (1991).

The expression "chronic pain", as used herein refers to intractable pain of prolonged duration. The etiology of chronic pain is varied. Sources include cancer, bone degenerating disorders, neuropathies, autoimmune disorders, arthritis and other inflammatory diseases, gastrointestinal disorders, such as ulcerative colitis and Crohn's diseases, injuries and the like.

The expression "female-specific pain", as used herein, refers to pain which, due to anatomical and/or physiological differences between the sexes, occurs only in women, or pain that has been clinically determined to be experienced to a greater degree by women than by men. Thus, female-specific pain includes not only pain that results from menstruation, ovulation, pregnancy and/or childbirth, but also pain due to miscarriage, ectopic pregnancy, rupture of a follicular or corpus luteum cyst, retrograde menstruation, chemical irritation of the pelvic viscera, uterine fibroids, adenomyosis, endometriosis, infection and inflammation, ischemia of a pelvic organ, obstruction, intra-abdominal adhesions, anatomic distortion of the pelvic viscera, ovarian absess, loss of pelvic support, tumors, pelvic congestion or referred pain from non-gynecological causes.

The method of the present invention may also be used to advantage to treat migraine symptoms in females. While migraine pain is not female-specific, the compounds of the invention should effectively alleviate migraine pain in females at lower doses than those required for treatment of the same condition in males.

While not wishing to be confined to a particular theory, it is believed that the number of nicotine acetylcholine receptors (nAChR) is greater in females than in males. Therefore, the administration of nAChR agonists tend to produce greater analgesic effects in females than in males.

The present invention provides a method for providing relief from chronic and/or female specific pain to a subject susceptible to such a conditions or disorders, and for providing treatment to a subject suffering therefrom. For example, the method comprises administering to a patient an amount of a compound effective for providing some degree of relief from pain (i.e., provide protective effects), amelioration of the symptoms of a disorder, and amelioration of the recurrence of a disorder. The method involves administering an effective amount of a compound selected from the general formulae which are set forth hereinbefore. The present invention also provides a pharmaceutical composition incorporating a compound selected from the general formulae which are set forth hereinbefore. Optically active compounds can be employed as racemic mixtures or as enantiomers. The compounds can be employed in a free base form or in a salt form (e.g., as pharmaceutically acceptable salts). Examples of suitable pharmaceutically acceptable salts include inorganic acid addition salts such as hydrochloride, hydrobromide, sulfate, phosphate, and nitrate; organic acid addition salts such as acetate, galactarate, propionate, succinate, lactate, glycolate, malate, tartrate, citrate, maleate, fumarate, methanesulfonate, p- toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or ethanol solvates. Representative salts are provided as described in U.S. Pat. No. 5,597,919 to Dull et al., U.S. Pat. No. 5,616,716 to Dull et al. and U.S. Pat. No. 5,663,356 to Ruecroft et al.

The pharmaceutical composition also can include various other components as additives or adjuncts. Exemplary pharmaceutically acceptable components or adjuncts which are employed in relevant circumstances include antioxidants, free radical scavenging agents, peptides, growth factors, antibiotics, bacteriostatic agents, immunosuppressives, anticoagulants, buffering agents, anti-inflammatory agents, anti-pyretics, time release binders, anaesthetics, steroids and corticosteroids. Such components can provide additional therapeutic benefit, act to effect the therapeutic action of the pharmaceutical composition, or act towards preventing any potential side effects which may be posed as a result of administration of the pharmaceutical composition. In certain circumstances, a compound of the present invention can be employed as part of a pharmaceutical composition with other compounds intended to prevent or treat a particular disorder.

The manner in which the compounds are administered can vary. The compounds can be administered by inhalation (e.g., in the form of an aerosol either nasally or using delivery articles of the type set forth in U.S. Pat. No. 4,922,901 to Brooks et al.); topically (e.g., in lotion form); orally (e.g., in liquid form within a solvent such as an aqueous or non-aqueous liquid, or within a solid carrier); intravenously (e.g., within a dextrose or saline solution); as an infusion or injection (e.g., as a suspension or as an emulsion in a pharmaceutically acceptable liquid or mixture of liquids); intrathecally; intracerebro ventricularly; or transdermally (e.g., using a transdermal patch). Although it is possible to administer the compounds in the form of a bulk active chemical, it is preferred to present each compound in the form of a pharmaceutical composition or formulation for efficient and effective administration. Exemplary methods for administering such compounds will be apparent to the skilled artisan. For example, the compounds can be administered in the form of a tablet, a hard gelatin capsule or as a time release capsule. As another example, the compounds can be delivered transdermally using the types of patch technologies available from Novartis and Alza Corporation. The administration of the pharmaceutical compositions of the present invention can be intermittent, or at a gradual, continuous, constant or controlled rate to a warm-blooded animal, (e.g., a mammal such as a mouse, rat, cat, rabbit, dog, pig, cow, or monkey); but advantageously is preferably administered to a human being. In addition, the time of day and the number of times per day that the pharmaceutical formulation is administered can vary. Administration preferably is such that the active ingredients of the pharmaceutical formulation interact with receptor sites within the body of human subject associated with a chronic or female-specific pain disorder. More specifically, in treating a chronic or female-specific pain, administration preferably is such so as to optimize the effect upon those relevant receptor subtypes involved in the etiology of the pain, while minimizing the effects upon muscle-type receptor subtypes. Other suitable methods for administering the compounds of the present invention are described in U.S. Pat. No. 5,604,231 to Smith et al., the disclosure of which is incorporated herein by reference in its entirety.

The appropriate dose of the compound is that amount effective to prevent occurrence of the symptoms of the disorder or to treat some symptoms of the disorder from which the patient suffers. By "effective amount", "therapeutic amount" or "effective dose" is meant that amount sufficient to elicit the desired pharmacological or therapeutic effects, thus resulting in effective prevention or treatment of the disorder. Prevention of the disorder is manifested by delaying the onset of the symptoms of the disorder. Treatment of the disorder is manifested by a decrease in the symptoms associated with the disorder or an amelioration of the recurrence of the symptoms of the disorder. Relative to (E)-metanicotine, compounds of the present invention are less extensively metabolized (i.e., fewer metabolites are formed, and the rate of elimination from blood is slower) in mammalian systems.

The effective dose can vary, depending upon factors such as the condition of the patient, the severity of the symptoms of the disorder, and the manner in which the pharmaceutical composition is administered. For human patients, the effective dose of typical compounds generally requires administering the compound in an amount sufficient to activate relevant receptors to effect neurotransmitter (e.g., dopamine) release but the amount should be insufficient to induce effects on skeletal muscles and ganglia to any significant degree. The effective dose of compounds will of course differ from patient to patient but in general includes amounts starting where chronic or female-specific pain is ameliorated or other desired therapeutic effects occur, but below the amount where muscular effects are observed.

Typically, the effective dose of compounds generally requires administering the compound in an amount of less than 5 mg/kg of patient weight. Often, the compounds of the present invention are administered in an amount from 1 mg to less than 100 μg/kg of patient weight, frequently between about 10 μg to less than 100 μg/kg of patient weight, and preferably between about 10 μg to about 50 μg/kg of patient weight. For compounds of the present invention that do not induce effects on muscle type nicotinic receptors at low concentrations, the effective dose is less than 5 mg/kg of patient weight; and often such compounds are administered in an amount from 50 μg to less than 5 mg/kg of patient weight. The foregoing effective doses typically represent that amount administered as a single dose, or as one or more doses administered over a 24 hour period.

For human patients, the effective dose of typical compounds generally requires administering the compound in an amount of at least about 1, often at least about 10, and frequently at least about 25 μg/24 hr./patient. For human patients, the effective dose of typical compounds requires administering the compound which generally does not exceed about 500, often does not exceed about 400, and frequently does not exceed about 300 μg/24 hr./patient. In addition, administration of the effective dose is such that the concentration of the compound within the plasma of the patient normally does not exceed 500 ng/ml, and frequently does not exceed 100 ng/ml.

The compounds useful according to the method of the present invention have the ability to pass across the blood-brain barrier of the patient. As such, such compounds have the ability to enter the central nervous system of the patient. The log P values of typical compounds, which are useful in carrying out the present invention are generally greater than about 0, often are greater than about 0.5, and frequently are greater than about 1. The log P values of such typical compounds generally are less than about 3.5, often are less than about 3, and sometimes are less than about 2.5. Log P values provide a measure of the ability of a compound to pass across a diffusion barrier, such as a biological membrane. See, Hansch, et al., *J. Med. Chem.* 11:1 (1968).

The compounds useful according to the method of the present invention have the ability to bind to, and in most circumstances, cause activation of, nicotinic cholinergic receptors of the brain of the patient (e.g., such as those receptors that modulate dopamine release). As such, such compounds have the ability to express nicotinic pharmacology, and in particular, to act as nicotinic agonists. The receptor binding constants of typical compounds useful in carrying out the present invention generally exceed about 0.1 nM, often exceed about 1 nM, and frequently exceed about 10 nM. The receptor binding constants of such typical compounds generally are less than about 1 μM, often are less than about 100 nM, and frequently are less than about 50 nM. Receptor binding constants provide a measure of the ability of the compound to bind to half of the relevant receptor sites of certain brain cells of the patient. See, Cheng, et al., *Biochem. Pharmacol.* 22:3099 (1973).

The compounds useful according to the method of the present invention have the ability to demonstrate a nicotinic function by effectively eliciting ion flux through, and/or neurotransmitter secretion from, nerve ending preparations (e.g., thalamic or striatal synaptosomes). As such, such compounds have the ability to cause relevant neurons to become activated, and to release or secrete acetylcholine, dopamine, or other neurotransmitters. Generally, typical compounds useful in carrying out the present invention effectively provide for relevant receptor activation in amounts of at least about 30 percent, often at least about 50 percent, and frequently at least about 75 percent, of that maximally provided by (S)-(−)-nicotine. Generally, typical compounds useful in carrying out the present invention are more potent than (S)-(−)-nicotine in eliciting relevant receptor activation. Generally, typical compounds useful in carrying out the present invention effectively provide for the secretion of dopamine in amounts of at least about 50 percent, often at least about 75 percent, and frequently at least about 100 percent, of that maximally provided by (S)-(−)-nicotine. Certain compounds of the present invention can provide secretion of dopamine in an amount which can exceed that maximally provided by (S)-(−)-nicotine. Generally, typical compounds useful in carrying out the present invention are less potent than (S)-(−)-nicotine in eliciting neurotransmitter secretion, such as dopamine secretion.

The compounds of the present invention, when employed in effective amounts in accordance with the method of the present invention, lack the ability to elicit activation of nicotinic receptors of human muscle to any significant degree. In that regard, the compounds of the present invention demonstrate poor ability to cause isotopic rubidium ion flux through nicotinic receptors in cell preparations expressing muscle-type nicotinic acetylcholine receptors. Thus, such compounds exhibit receptor activation constants or EC50 values (i.e., which provide a measure of the concentration of compound needed to activate half of the relevant receptor sites of the skeletal muscle of a patient) which are extremely high (i.e., greater than about 100 μM). Generally, typical preferred compounds useful in carrying the present invention activate isotopic rubidium ion flux by less than 10 percent, often by less than 5 percent, of that maximally provided by S(−) nicotine.

The compounds of the present invention, when employed in effective amounts in accordance with the method of the present invention, are selective to certain relevant nicotinic receptors, but do not cause significant activation of receptors associated with undesirable side effects. By this is meant that a particular dose of compound resulting in prevention and/or treatment of female specific pain and/or chronic pain, is essentially ineffective in eliciting activation of certain ganglionic-type nicotinic receptors. This selectivity of the compounds of the present invention against those receptors responsible for cardiovascular side effects is demonstrated by a lack of the ability of those compounds to activate nicotinic function of adrenal chromaffin tissue. As such, such compounds have poor ability to cause isotopic rubidium ion flux through nicotinic receptors in cell preparations derived from the adrenal gland. Generally, typical preferred compounds useful in carrying out the present invention activate isotopic rubidium ion flux by less than 10 percent, often by less than 5 percent, of that maximally provided by S(−) nicotine.

Compounds of the present invention, when employed in effective amounts in accordance with the method of the present invention, are effective towards providing some degree of prevention or amelioration of chronic pain, female specific pain, and to some degree of the recurrence of such pain. However, such effective amounts of those compounds are not sufficient to elicit any appreciable side effects, as is demonstrated by decreased effects on preparations believed to reflect effects on the cardiovascular system, or effects to skeletal muscle. As such, administration of compounds of the present invention provides a therapeutic window in which treatment of chronic and female specific pain and side effects are avoided. That is, an effective dose of a compound of the present invention is sufficient to provide the desired effects upon amelioration of pain, particularly in females, but is insufficient (i.e., is not at a high enough level) to provide undesirable side effects. Preferably, effective administration of a compound of the present invention resulting in treatment of female specific and/or chronic pain occurs upon administration of less than ⅓, frequently less than ⅕, and often less than ⅒, that amount sufficient to cause any side effects to a significant degree.

The following examples are provided to describe the invention in further detail. The examples are intended merely to illustrate and not to limit the invention.

Example I describes a study which was carried out to assess the analgesic efficacy of intrathecal administration of the compounds of the invention in female and male rats.

EXAMPLE I

Trans-metanicotine was administered via intrathecal catheters inserted in male and female Sprague Dawley rats such that their tips were in the upper lumbar region. Analgesia was determined as an increase in the latency to withdrawal of the hindpaw from a focused light heat source. To prevent injury, duration of 30 seconds was not exceeded. The latency to paw withdrawal was determined both before and after intrathecal injection of trans-metanicotine in these rats, and the data were expressed as % maximum possible effect.

This study demonstrated that in male and female rats, the i.t. injection of trans-metanicotine produced a dose dependent inhibition of paw withdrawal latency to a radiant heat stimulus up to a dose of 20 µg, whereas 60 µg failed to be more effective. The antinociceptive response, which lasted for about 10 minutes, was twice as great in the females than in the males, with a maximum possible analgesic effect of 45% and 20%, respectively. These data demonstrate that trans-metanicotine produces spinal analgesia in rats with a clear ceiling effect. Furthermore, these results tend to indicate an increased sensitivity to intrathecally administered nicotinic acetylcholine receptor agonists in female compared to male rats.

EXAMPLE II

Analgesic potency of compounds of the present invention can also be tested in animal models of neuropathic or neurogenic pain. One such model resembles the human condition termed causalgia or reflex sympathetic dystrophy (RSD) secondary to injury of a peripheral nerve. This condition is characterized by hyperesthesia (enhanced sensitivity to a natural stimulus), hyperalgesia (abnormal sensitivity to pain), allodynia (hypersensitivity and pain to normally non-painful stimuli, either thermal or tactile), and spontaneous burning pain. In humans, neuropathic pain tends to be chronic and may be debilitating.

This type of pain is generally considered to be non-responsive or only partially responsive to conventional opioid analgesic regimens (Jadad, A. R. et al. (1992) Lancet 339:1367-1371). In accordance with the invention, analgesic metanicotine compounds and analogs thereof are effective in providing relief of neuropathic pain, as described in the following paragraphs.

Briefly, in the model used, rats are subjected to a surgical procedure, described by Kim et al. (Kim, S. H. and Chung, J. M. (1992) Pain 50:355–363), designed to reproducibly injure peripheral nerves (spinal nerves L5 and L6). These rats develop a hyperesthetic state, which can be measured, using one or more paradigms known in the art. Here, allodynia was measured by stimulation of neuropathic rat hindlimb using nylon filaments having graded degrees of stiffness.

Sex differences in response to (E)-N-methyl-4-(3-pyridinyl)-3-butene-1-amine were tested using the assay described above. Hypersensitivity to light touch (withdrawal threshold to application of calibrated von Frey filaments) was documented one week later. Intrathecal injection of (E)-N-methyl-4-(3-pyridinyl)-3-butene-1-amine had no effect in males, but returned the level of sensitivity 50±4% (mean ±SEM) to presurgery levels, after 100 µg in females.

EXAMPLE III

Adult male and female Sprague Dawley rats were prepared with insertion of intrathecal catheters as described above. Capsaicin (8-methyl-N-vanillyl nonamide) was prepared in a concentration of 30 µg in 10 µl. Briefly, capsaicin powder was first dissolved in Tween 80, then in isotonic saline and heated to 70° C. The solution obtained was filtered and stored in sterile glass vials. Each group of rats represents 6 males and 6 females tested at the same time and each animal received only one injection in the left plantar surface of the hindpaw. Each animal was lightly anesthetized under halothane and immediately after immobility, received intradermal capsaicin, 30 µg injected through a 28 G needle, in the center of the plantar surface. This dose was chosen because it produces mechanical hyperalgesia lasting at least 2 hours (Gilchrist, H. D., Allard, B. L., and Simone, D. A. Enhanced withdrawal responses to heat and mechanical stimuli following intraplantar injection of capsaicin in rats. Pain 1996;67: 179–188).

Recovery from anesthesia was rapid and all the animals displayed a nocifensive behavior lasting less than 5 minutes, then behaved normally and used the paw for locomotion. Hindpaw withdrawal thresholds were tested before capsaicin injection and every 30 minutes thereafter for 2 hours, using von Frey filaments and the up-down method described above. Care was taken to avoid direct contact of the injection point when measuring withdrawal threshold with the filaments. Intrathecal saline, or (E)-N-methyl-4-(3-pyridinyl)-3-butene-1-amine(50 µg) was injected prior to capsaicin.

Intraplantar injection of capsaicin produced a rapid onset, sustained reduction in withdrawal threshold in both sexes. However, male and female control animals differed in withdrawal threshold at baseline and after capsaicin, and the sexes were therefore compared by % change from pre-capsaicin threshold. By this analysis, the average % reduction in withdrawal threshold over the 2 hours after capsaicin injection was 74+/−5.3% in females and 64+/−6.7% in males (p=0.47, NS). Thus,(E)-N-methyl-4-(3-pyridinyl)-3-butene-1-amine produced analgesia in this model of pain which was similar between the sexes.

Several U.S. patents and scientific references are referred to in the foregoing specification. The entire disclosure of each is incorporated by reference in the present specification as though set forth herein in full.

While certain embodiments of the present invention have been described and exemplified above, various other embodiments will be apparent to those skilled in the art from the foregoing disclosure. For example, it is believed that the homologs and analogs of metanicotine as described in the above-mentioned patents, which also function as nicotonic acetylcholine receptor agonists, are likewise therapeutically effective in treating female-specific and/or chronic pain. The present invention is, therefore, not limited to the particular embodiment specifically described and exemplified, but is capable of considerable variation and modification without departure from the scope of the appended claims.

What is claimed is:

1. A method for treating female-specific pain in a female patient in need of said treatment by administering a therapeutically effective amount of a compound having the formula:

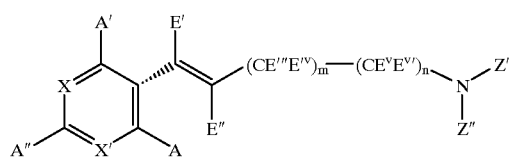

(I)

wherein X is nitrogen or carbon bonded to a substituent species having a sigma m value greater than 0 or less than 0; X' is nitrogen; A, A' and A" individually represent substituent species characterized as having a sigma m value greater than 0, less than 0, or 0; m is an integer and n is an integer such that the sum of m plus n is 1, 2, 3, 4, 5, 6, 7, or 8; $E^I$, $E^{II}$, $E^{III}$, $E^{IV}$, $E^V$ and $E^{VI}$ individually represent hydrogen, lower alkyl, including $C_1$–$C_8$, or halo substituted lower alkyl, including $C_1$–$C_8$; and Z and Z" individually represent hydrogen or lower alkyl; the wavy line in formula I indicating that the compound can have a cis(Z) or trans (E) form; and the pharmaceutically acceptable salts of said compound.

2. A method as claimed in claim 1, wherein the compound is administered in the E form; Z' is hydrogen or methyl and Z" is hydrogen; $E^I$, $E^{II}$ are each hydrogen; $E^{III}$, $E^{IV}$ and $E^V$ are hydrogen and $E^{VI}$ is methyl; A, A' and A" are each hydrogen and m+n=2 or 3.

3. A method as claimed in claim 1, wherein Z' in said compound individually represents hydrogen or methyl and Z" in said compound is hydrogen.

4. A method as claimed in claim 1, wherein said compound is in its E form and E' and E" in said compound are each hydrogen.

5. A method as claimed in claim 1, wherein said compound is in its Z form and E' and E" in said compound are each hydrogen.

6. A method as claimed in claim 1, wherein $E^{III}$, $E^{IV}$ and $E^V$ in said compound are each hydrogen and E" in said compound is methyl.

7. A method as claimed in claim 1, wherein A, A' and A" in said compound are hydrogen.

8. A method as claimed in claim 1, wherein $E^I$, $E^{II}$, $E^{III}$, $E^{IV}$, $E^V$ and $E^{VI}$ each represent hydrogen.

9. A method as claimed in claim 1, wherein A is hydrogen.

10. A method as claimed in claim 1, wherein at least one of Z' and Z" is hydrogen.

11. A method as claimed in claim 1, wherein m+n in said compound=2 or 3.

12. A method as claimed in claim 1, wherein m+n in said compound=3.

13. A method as claimed in claim 1, wherein said compound is administered in the form of its trans isomer.

14. A method as claimed in claim 1, wherein said compound is administered in an amount ranging from about 0.005 to about 0.5 mg/kg of patient body weight per day.

15. A method as claimed in claim 1, wherein said female-specific pain is pain resulting from menstruation.

16. A method as claimed in claim 1, wherein said female-specific pain is pain resulting from ovulation.

17. A method as claimed in claim 1, wherein said female-specific pain is pain resulting from pregnancy.

18. A method as claimed in claim 1, wherein said female-specific pain is pain resulting from childbirth.

19. A method for treating chronic pain in a patient in need of said treatment by administering a therapeutically effective amount of a compound having the formula:

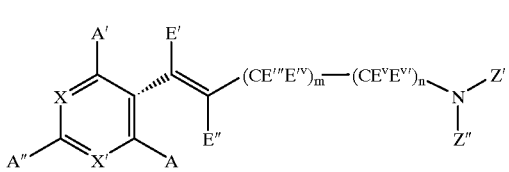

(I)

wherein X is nitrogen or carbon bonded to a substituent species having a sigma m value greater than 0 or less than 0; X' is nitrogen; A, A' and A" individually represent substituent species characterized as having a sigma m value greater than 0, less than 0, or 0; m is an integer and n is an integer such that the sum of m plus n is 1, 2, 3, 4, 5, 6, 7, or S; $E^I$, $E^{II}$, $E^{III}$, $E^{IV}$, $E^V$ and $E^{VI}$ individually represent hydrogen, lower alkyl, including $C_1$–$C_8$, or halo substituted lower alkyl, including $C_1$–$C_8$; and Z and Z" individually represent hydrogen or lower alkyl and the pharmaceutically acceptable salts of said compound.

20. A method as claimed in claim 19, wherein the compound is administered in the E form; Z' is hydrogen or methyl and Z" is hydrogen; $E^I$, $E^{II}$ are each hydrogen; $E^{III}$, $E^{IV}$ and $E^V$ are hydrogen and $E^{VI}$ is methyl; A, A' and A" are each hydrogen and m+n=2 or 3.

21. A method as claimed in claim 19, wherein Z' in said compound individually represents hydrogen or methyl and Z" in said compound is hydrogen.

22. A method as claimed in claim 19, wherein said compound is in its E form and E' and E" in said compound are each hydrogen.

23. A method as claimed in claim 19, wherein said compound is in its Z form and E' and E" in said compound are each hydrogen.

24. A method as claimed in claim 19, wherein $E^{III}$, $E^{IV}$ and $E^V$ in said compound are each hydrogen and $E^{VI}$ in said compound is methyl.

25. A method as claimed in claim 19, wherein A, A' and A" in said compound are hydrogen.

26. A method as claimed in claim 19, wherein $E^I$, $E^{II}$, $E^{III}$, $E^{IV}$, $E^V$ and $E^{VI}$ each represent hydrogen.

27. A method as claimed in claim 19, wherein A is hydrogen.

28. A method as claimed in claim 19, wherein at least one of Z' and Z" is hydrogen.

29. A method as claimed in claim 19, wherein m+n in said compound=2 or 3.

30. A method as claimed in claim 19, wherein m+n in said compound=3.

31. A method as claimed in claim 19, wherein said compound is administered in the form of its trans isomer.

32. A method as claimed in claim 19, wherein said compound is administered in an amount ranging from about 0.005 to about 0.5 mg/kg of patient body weight oer day.

33. A method as claimed in claim 19 wherein said chronic pain is pain resulting from cancer.

34. A method as claimed in claim 19 wherein said chronic pain is pain resulting from a bone degerative disease.

35. A method as claimed in claim 19, wherein said chronic pain is pain resulting from arthritis.

36. A method as claimed in claim 19, wherein said chronic pain is pain resulting from injury.

\* \* \* \* \*